(12) United States Patent
Mimura et al.

(10) Patent No.: US 8,902,306 B2
(45) Date of Patent: *Dec. 2, 2014

(54) METHOD FOR DETECTING CELL STATES, AND IMAGE PROCESSING DEVICE FOR CELL VIEWING

(75) Inventors: Masafumi Mimura, Ageo (JP); Kei Ito, Okegawa (JP)

(73) Assignee: Nikon Corporation, Tokyo (JP)

( * ) Notice: Subject to any disclaimer, the term of this patent is extended or adjusted under 35 U.S.C. 154(b) by 798 days.

This patent is subject to a terminal disclaimer.

(21) Appl. No.: 12/929,369

(22) Filed: Jan. 19, 2011

(65) Prior Publication Data

US 2011/0228069 A1    Sep. 22, 2011

Related U.S. Application Data

(63) Continuation of application No. PCT/JP2009/003318, filed on Jul. 15, 2009.

(30) Foreign Application Priority Data

Jul. 23, 2008    (JP) .................................. 2008-189995

(51) Int. Cl.
| | | |
|---|---|---|
| H04N 7/18 | (2006.01) | |
| G06K 9/00 | (2006.01) | |
| G02B 21/00 | (2006.01) | |
| G02B 21/36 | (2006.01) | |
| G06T 7/40 | (2006.01) | |
| C12M 1/34 | (2006.01) | |
| C12M 3/00 | (2006.01) | |
| C12M 1/00 | (2006.01) | |
| G06T 7/00 | (2006.01) | |
| G06T 7/20 | (2006.01) | |
| G06K 9/62 | (2006.01) | |

(52) U.S. Cl.
CPC .......... *G02B 21/365* (2013.01); *G02B 21/0088* (2013.01); *G06T 7/401* (2013.01); *G06T 2207/10056* (2013.01); *C12M 41/36* (2013.01); *C12M 41/46* (2013.01); *C12M 23/48* (2013.01); *G96K 9/00147* (2013.01); *C12M 41/14* (2013.01); *G06T 7/0012* (2013.01); *G06T 7/20* (2013.01); *G06T 7/0028* (2013.01); *G06T 2207/30024* (2013.01); *G06T 7/0016* (2013.01)
USPC .............................. 348/79; 382/133; 382/216

(58) Field of Classification Search
CPC .............. C12M 23/48; G06K 9/00147; G06T 2207/30024; G06T 2207/10056; G02B 21/365; G02B 21/367
See application file for complete search history.

(56) References Cited

U.S. PATENT DOCUMENTS

2002/0110928 A1    8/2002  Yahiro
2003/0185450 A1*  10/2003  Garakani et al. .............. 382/232
(Continued)

FOREIGN PATENT DOCUMENTS

JP    2002-214228    7/2002
JP    2004-229619    8/2004
(Continued)

OTHER PUBLICATIONS

Yanhua Hu et al., Application of Temporal Texture Features to Automated Analysis of Protein Subcellular Locations in Time Series Fluorescence Microscope Images:, Biomedical Imaging: Macro to Nano, 2006. 3rd IEEE International Symposium on Apr. 6, 2006, Piscataway, NJ, USA, IEEE, pp. 1028-1031.

(Continued)

*Primary Examiner* — Behrooz Senfi
*Assistant Examiner* — Mohammed Jebari
(74) *Attorney, Agent, or Firm* — Staas & Halsey LLP

(57) ABSTRACT

An image processing device determines the degree of activity of a cell during cell viewing. An imaging device captures first and second images of a cell under observation. After aligning the rotational angle orientations on the image plane of the cell under observation that is included in the images, a correlation value or difference of intracellular texture feature values in the first image and second image, is sequentially computed. A time series variation of the computed correlation value or difference is then derived, and the degree of activity of the cell under observation is detected based on the state of variation.

11 Claims, 8 Drawing Sheets

(56) References Cited

U.S. PATENT DOCUMENTS

| | | |
|---|---|---|
| 2006/0039593 A1* | 2/2006 | Sammak et al. ............... 382/133 |
| 2006/0073470 A1 | 4/2006 | Noda et al. |
| 2007/0031818 A1* | 2/2007 | Kutsyy et al. ..................... 435/4 |
| 2008/0247628 A1* | 10/2008 | Ramsing et al. ............... 382/133 |
| 2009/0086314 A1 | 4/2009 | Namba et al. |
| 2010/0111354 A1* | 5/2010 | Hornabrook et al. ......... 382/100 |

FOREIGN PATENT DOCUMENTS

| | | |
|---|---|---|
| JP | 2007-155982 | 6/2007 |
| KR | 10-2005-0062543 A | 6/2005 |
| WO | 03/100086 A1 | 12/2003 |
| WO | 03/102224 A1 | 12/2003 |
| WO | 2004/020656 A1 | 3/2004 |
| WO | 2007/139201 A1 | 6/2007 |
| WO | 2009/110462 A1 | 9/2009 |

OTHER PUBLICATIONS

Extended European Search Report dated Nov. 12, 2012 in European Application No. 09800187.8-2218.

Yukari Sasamura et al., "A note on an Automatic Extract Method for Apoptoic Cells from Videomicroscopy Images," School of Engineering, Hokkaido University, ITE Technical Report vol. 27, No. 38, Jul. 2003, pp. 21-24.

International Search Report for PCT/JP2009/003318 mailed Oct. 13, 2009.

* cited by examiner

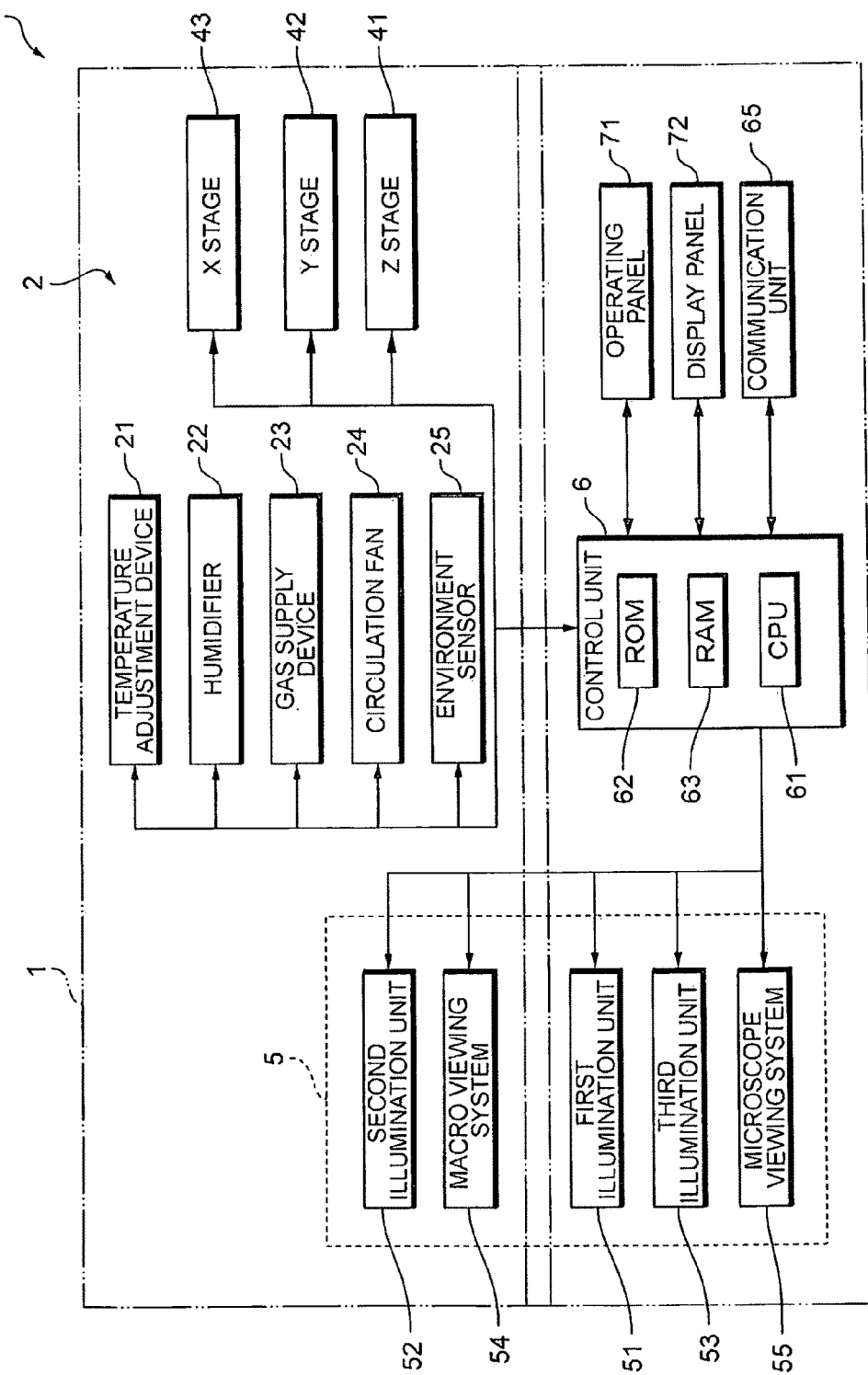

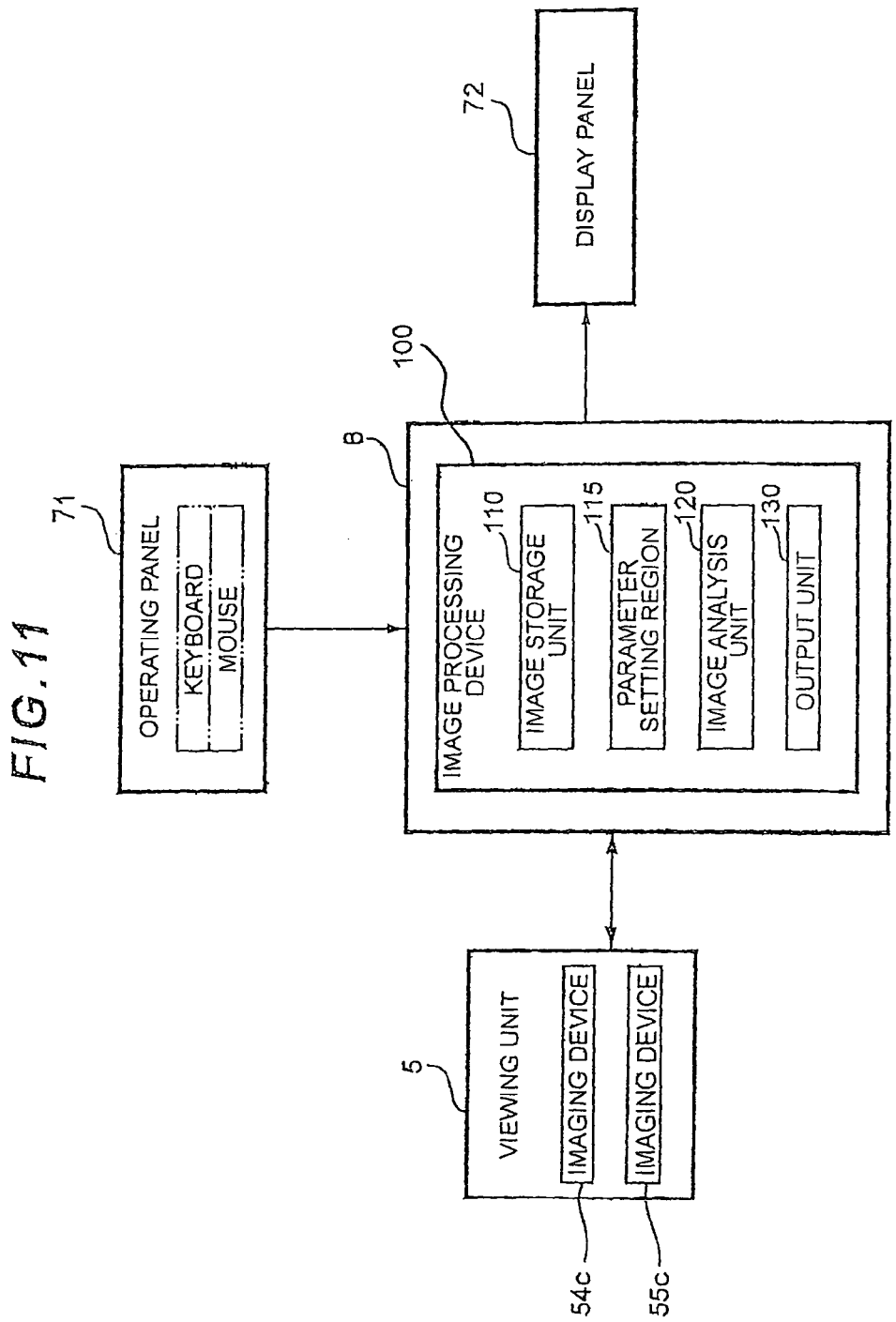

METHOD FOR DETECTING CELL STATES, AND IMAGE PROCESSING DEVICE FOR CELL VIEWING

CROSS REFERENCE TO RELATED APPLICATIONS

This application is a continuation application, filed under 35 U.S.C. §111(a), of International Application PCT/JP2009/003318, filed Jul. 15, 2009, which claimed priority to Japanese Application No. 2008-189995, filed Jul. 23, 2008, the disclosures of which are hereby incorporated by reference.

TECHNICAL FIELD

The present invention relates to a method for detecting a cell state, whereby the degree of activity of a cell is detected from an image obtained in cell viewing.

TECHNICAL BACKGROUND

A culture microscope is an example of a device for observing a cell. A culture microscope is provided with a culture device for forming an environment suitable for culturing a cell, and a microscope viewing system for microscopic viewing of a cell in a culture container, and the culture microscope is configured so that changes, divisions, and other cell activities can be observed while the living cell is cultured (see Japanese Laid-open Patent Publication No. 2004-229619 for example). In a conventional cell viewing method using such a culture microscope, the state of life or death, degree of activity, and other features of the cell under observation are determined by reagent determination, template matching, or visual observation.

SUMMARY THE INVENTION

However, the conventional method such as described above has drawbacks in that the culture state of the cell is affected by the administration of reagents to the culture container, a bulky template is required for determination of cell transformations/variations using a template, and a large processing burden is involved, and accurate determinations are difficult to make by visual observation.

The present invention was developed in view of such problems as the foregoing, and an object of the present invention is to provide a means whereby cell activity can be accurately determined from an observation image taken by an imaging device.

According to an aspect of the present invention, there is provided a method for detecting a cell state, comprising the steps of sequentially obtaining first image data and second image data in which a cell under observation is captured by an imaging device at a predetermined time interval; aligning the rotation angle orientations of the cell under observation with each other on the basis of the first and second image data; extracting a variation amount between an intracellular texture feature value of the cell under observation in the first image data and an intracellular texture feature value of the cell under observation in the second image data, the rotation angle orientations of the cell under observation being aligned; and detecting a degree of activity of the cell under observation on the basis of a time series variation of the extracted variation amount.

According to a second aspect of the present invention, there is provided an image processing device for cell viewing, comprising imaging means for capturing a cell; image obtaining means for sequentially obtaining first image data and second image data in which a cell under observation is captured by an imaging device at a predetermined time interval; rotation angle orientation control means for aligning the rotation angle orientations of the cell under observation with each other on the basis of the first and second image data; and image analyzing means for extracting a variation amount between an intracellular texture feature value of the cell under observation in the first image data and an intracellular texture feature value of the cell under observation in the second image data, the rotation angle orientations of the cell under observation being aligned; and detecting a degree of activity of the cell under observation on the basis of a time series variation of the extracted variation amount.

In the image processing device for cell viewing, a configuration is preferably adopted in which the image analyzing means is configured so as to detect the degree of activity of the cell under observation on the basis of the time series variation of the correlation value or the difference, and output the degree of activity of the cell under observation that is detected by the image analyzing means.

Advantageous Effects of the Invention

Through a cell state detection method and image processing device for cell viewing such as described above, the degree of activity of a cell under observation is detected by the time series variation of the correlation or difference between texture features of the cell under observation from one predetermined time to the next. Consequently, a means can be provided which makes it possible to accurately determine the activity of a cell from observation images captured and obtained by an imaging device.

BRIEF DESCRIPTION OF THE DRAWINGS

FIG. 3 is a block diagram showing the culture viewing system;

FIG. 11 is a block diagram showing the overall configuration of the image processing device.

DESCRIPTION OF EMBODIMENTS

Figure 2:
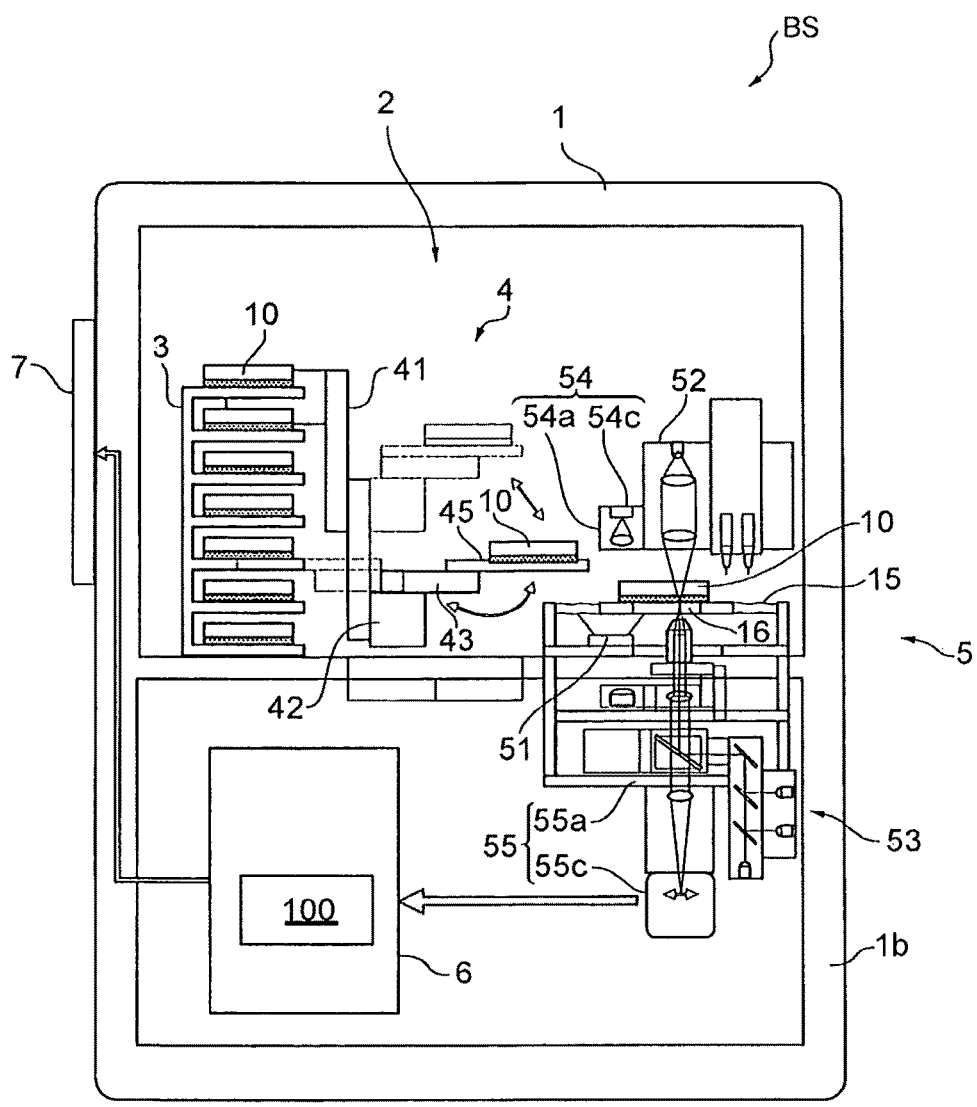
FIG. 2 is a rough structural view showing a culture viewing system described as an application of the present invention.

Embodiments of the present invention will be described hereinafter with reference to the drawings. FIGS. 2 and 3 are a rough structural view and a block diagram, respectively, showing a culture viewing system as an example of a system to which the image processing device for cell viewing according to the present invention is applied.

The culture viewing system BS is primarily composed of a culture chamber 2 provided at the top of a chassis 1; a shelved stocker 3 for accommodating and retaining a plurality of culture containers 10; a viewing unit 5 for observing samples in the culture containers 10; a conveyance unit 4 for conveying the culture containers 10 between the stocker 3 and the viewing unit 5; a control unit 6 for controlling the operation of the system; an operating board 7 provided with an image display device; and other components.

The culture chamber 2 is a room for forming a culture environment, and is kept sealed after a sample is introduced. The culture chamber 2 is additionally provided with such components as a temperature adjustment device 21, a humidifier 22, a gas supply device 23 for supplying $CO_2$ gas, $N_2$ gas, or other gas, a circulation fan 24, and an environment sensor 25 for detecting the temperature, humidity, and other features of the culture chamber 2. The stocker 3 is formed in a shelf shape having a plurality of divisions in the front-rear and up-down directions, and a specific number is set for each shelf. An appropriate culture container 10 is selected according to the type or purpose of the cell to be cultured, and cell samples are injected together with a liquid culture medium and retained in dish-type culture containers, for example. A code number is provided to each culture container 10, and each culture container 10 is associated with a designated number and accommodated in the stocker 3. The conveyance unit 4 is composed of such components as a Z stage 41 provided within the culture chamber 2 so as to be able to move up and down, a Y stage 42 attached so as to be able to move forward and backward, and an X stage 43 attached so as to be able to move left and right, and a support arm 45 for lifting and supporting a culture container 10 is provided toward the distal end of the X stage 43.

The viewing unit 5 is composed of such components as a first illumination unit 51 for providing backlight illumination of the entire culture container 10 from below a sample stage 15; a second illumination unit 52 for illuminating a sample in a culture container along the optical axis of a microscope viewing system 55 from above the sample stage 15; a third illumination unit 53 for illuminating the sample in the culture container along the optical axis of the microscope viewing system 55 from below the sample stage 15; a macro viewing system 54 for macro viewing of the sample; a microscope viewing system 55 for micro viewing of the sample; and an image processing device 100. A transparent window part 16 is provided to the sample stage 15 on which the culture container 10 is mounted, in the region thereof observed by the microscope viewing system 55.

The macro viewing system 54 has a viewing optical system 54a and a CCD camera or other imaging device 54c for capturing an image of a sample that is imaged by the viewing optical system, and the macro viewing system 54 is provided in the culture chamber 2 at a position above the first illumination unit 51. The macro viewing system 54 captures an overall observation image (macro image) from above the culture container 10 which is backlight-illuminated by the first illumination unit 51.

The microscope viewing system 55 has a viewing optical system 55a composed of an objective, a middle zooming lens, a fluorescence filter, and other components; and a cooled CCD camera or other imaging device 55c for capturing an image of the sample imaged by the viewing optical system 55a, and the microscope viewing system 55 is provided inside a lower frame 1b. A plurality of objectives and middle zooming lenses is provided, and configured so that a plurality of magnifications can be set by using a revolver, slider, or other displacement mechanism not shown in detail in the drawing. The microscope viewing system 55 captures a microscope observation image (micro image) in which transmitted light emitted by the second illumination unit 52 and transmitted by a cell, reflected light emitted by the third illumination unit 53 and reflected by a cell, or fluorescence emitted by a cell that is illuminated by the third illumination unit 53 is microscopically viewed.

The image processing device 100 processes signals inputted from the imaging device 54c of the macro viewing system and the imaging device 55c of the micro viewing system, and generates image data of the overall observation image or the micro observation image. The image processing device 100 applies image analysis to the image data of the observation images, and generates a time lapse image, analyzes the degree of activity of a cell, predicts a movement direction, analyzes the motion state of the cell, and performs other processing. The image processing device 100 will be described in detail hereinafter.

The control unit 6 has a CPU 61, a RCM 62 in which a control program, control data, or the like are set and stored for controlling the operation of the culture viewing system BS; a RAM 63 for temporarily storing image data and the like; and other components, and these components are connected by a data bus. The temperature adjustment device 21, humidifier 22, gas supply device 23, and other components in the culture chamber 2; the X, Y, and Z stages 43, 42, 41 in the conveyance unit 4; the first through third illumination units 51, 52, 53 in the viewing unit 5; the macro viewing system 54 and microscope viewing system 55; and an operating panel 71, a display panel 72, and other components in the operating board 7 are connected to an input/output port of the control unit 6. Detection signals from the components described above are inputted to the CPU 61, and the components described above are controlled in accordance with a control program.

The operating board 7 is provided with an operating panel 71 to which a keyboard, switch, optical disk reading device, or other input/output instrument is provided, and a display panel 72 for displaying an operating screen, image data, or the like, and by selecting settings or conditions of a viewing program and inputting operating commands and the like through the use of the operating panel 71 while referencing the display panel 72, the operation of each components of the culture viewing system BS is controlled via the CPU 61. The CPU 61 is capable of transmitting and receiving data with respect to an externally connected computer or the like via a communication unit 65 which is configured according to a wired or wireless communication standard. The RAM 63 stores environment conditions of the culture chamber 2, a viewing schedule, and viewing classifications, viewing positions, viewing magnifications, and other information for the viewing unit 5. The RAM 63 is also provided with an image data storage region for storing image data captured by the viewing unit 5, and index data which include a code number of the culture container 10, an image capture time, and other information are stored in association with image data.

In the culture viewing system BS thus generally configured, the CPU 61 controls the operation of each component on the basis of the control program stored in the ROM 62, and automatically captures the sample in the culture container 10, in accordance with the setting conditions of the viewing program set in the operating board 7. In other words, when the viewing program is started, the CPU 61 reads environment condition values stored in the RAM 63, and controls the operation of the temperature adjustment device 21, humidifier 22, and other components so that the culture environment matches the environment condition values. The CPU 61 also reads a viewing condition stored in the RAM 63, operates the X, Y, and Z stages 43, 42, 41 on the basis of the viewing schedule, conveys the culture container 10 to be viewed from the stocker 3 to the sample stage 15, and initiates viewing by the viewing unit 5. For example, in a case in which the viewing set in the viewing program is micro viewing of a cell in the culture container 10, the culture container 10 is positioned on the optical axis of the microscope viewing system 55, the light source of the second illumination unit 52 or the third illumination unit 53 is lit, and a micro observation image is captured by the imaging device 55c.

In viewing such as described above, the CPU 61 sequentially executes capture of the overall observation image or micro observation image according to a viewing schedule which is based on the viewing program. In the present embodiment, the observation images may be captured at a constant interval or at different intervals. The image data of the captured overall observation image or micro observation image are sequentially recorded in the image data storage region of the RAM 63 together with the capture time and other index data. The image data recorded in the RAM 63 are read from the RAM 63 in response to an image display command inputted from the operating panel 71, and the overall observation image or micro Observation image (single image) of a specified time, or a cell activity flag described hereinafter is displayed by the display panel 72.

In the culture viewing system BS configured as described above, the image processing device 100 has a function for displaying the degree of activity of a cell being viewed (cell under observation) so that the degree of activity can be determined, and this function is used for such purposes as cell culture analysis. The method for determining the degree of activity of a cell under observation will be described hereinafter in terms of the basic concept thereof.

(Extraction of Outermost Contour)

Figure 4A:
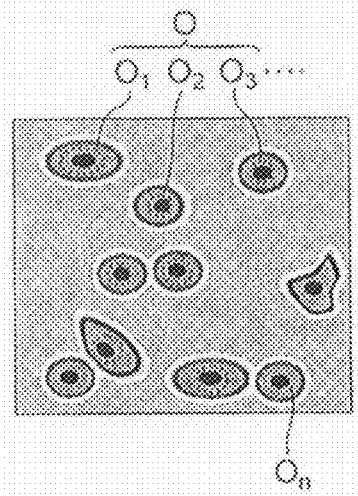
FIG. 4 is a schematic view showing an example of the conditions of contour extraction processing performed to extract the contours of cells.
Figure 4B:
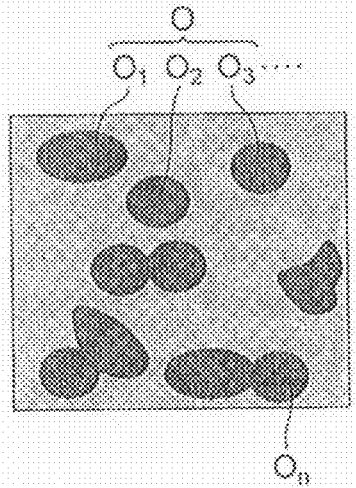

Prior to the specific processing for deriving the degree of activity, the outermost contours of cells O included in the image are extracted for an image (referred to as the first image, for the sake of convenience) captured at time t, and an image (referred to as the second image) captured at time t−1 a predetermined time before the first image. FIG. 4 is a schematic view showing the outermost contour extraction processing, and the outermost contours of the cells are extracted as shown in FIG. 4B, with respect to the image FIG. 4A obtained by the imaging device 55c (54c). Examples of methods for outermost contour extraction processing include applying a variance filter followed by binarization, dynamic contouring (Snakes, Level Set, and other methods), and other methods. The abovementioned predetermined time is set in accordance with the motion conditions of the cells in the viewing field, and is set to a time of about 10 minutes to one hour in cases in which cell motion is relatively active, and to about 30 minutes to two hours in cases in which the motion of living cells is relatively low.

Labeling is applied to each cell for which the outermost contour is extracted and segmented, and the cells $O_1$, $O_2$, $O_3$, ..., $O_n$ in the first image correspond to the cells $O_1'$, $O_2'$, $O_3'$, ..., $O_n'$ in the second image. For example, each cell in the first image is indicated by a solid line in FIG. 5, each cell in the second image is indicated by a dotted line, and the labeled cells correspond such that the labels nearest to each other indicate the same cell, where $O_1$ corresponds to $O_1'$, $O_2$ to $O_2'$, $O_3$ to $O_3'$, and so on with $O_n$ corresponding to $O_n'$.

(Adjustment of Rotation Angle Orientation)

The rotation angle orientations (azimuth directions of the cells) on the image plane of the figures (referred to as first figures) of the cells of the first image and the figures (referred to as second images) of the cells of the second image are then aligned for each of the corresponding cells. As a specific method for aligning the rotation angle orientations, a geometric moment of inertia (inertial moment) about an axis passing through the center of the centroid (center of gravity) is computed for associated cells, e.g., $O_1$ and $O_1'$, and the rotation angle orientations of the cells of the first figure and the second figure are aligned at the angle position of the maximum correlation value between the geometric moment of inertia $I_1$ of the first figure and the geometric moment of inertia $I_2$ of the second figure. In a case in which the contour shape of the cell is nearly circular, the correlation of the two figures is calculated while the first figure or second figure is rotated a certain angle at a time, and alignment occurs at the angle at which the correlation value is maximized.

A configuration may also be adopted in which the rotation angle orientations are aligned at the angle at which the difference between the geometric moment of inertia $I_1$ of the first figure and the geometric moment of inertia $I_2$ of the second figure is minimized, or a configuration may be adopted in which the difference is calculated while the first figure or second figure is rotated a certain angle at a time about an axis which passes through the centroid, and alignment occurs at the angle at which the difference between the first figure and the second figure is minimized. A configuration may also be adopted in which the cells O are approximated as ellipses, and the major-axis directions of the approximated ellipse models are aligned.

(Detection of Living Cells)

Figure 6:
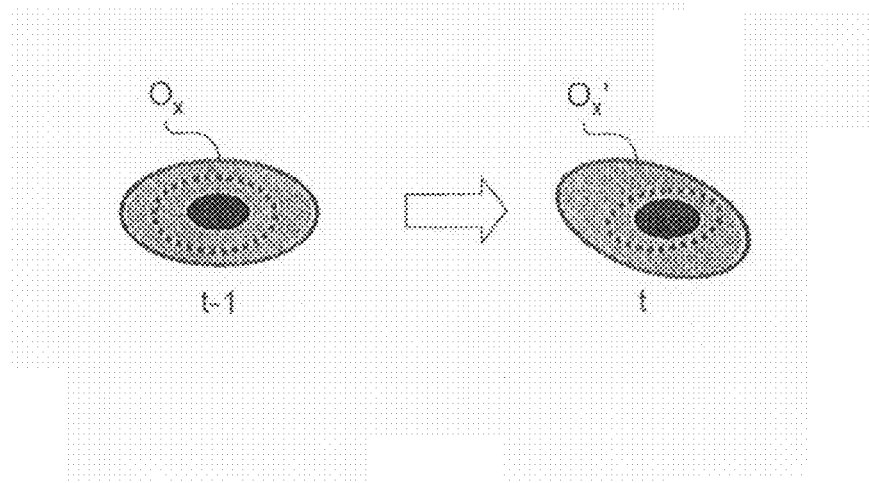
FIG. 6 is a schematic view showing an example of the change in a normal living cell from time t−1 to time t.
Figure 7:
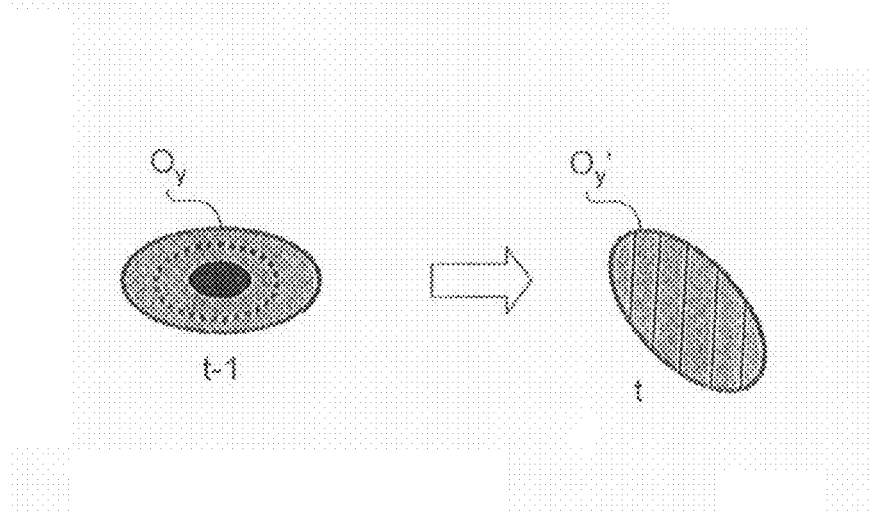
FIG. 7 is a schematic view showing an example of a change from a living cell to a dead cell from time t−1 to time t.

In a case in which a cell under observation as the subject of correlation calculation is a living cell, the shape as well as the internal structure thereof change over time from $O_x$ to $O_x'$, as shown in FIG. 6. The correlation value of the first figure and second figure is therefore not very large. On the other hand, in a case in which the cell under observation is debris, cell remains, or the like, there is almost no change in the shape and internal structure over time from $O_y$ to $O_y'$ as shown in FIG. 7. There is therefore a large correlation value for the first figure and second figure, for which the rotation angle orientations are aligned, and the correlation value is close to a value of 1.

Consequently, by aligning the rotation angle orientations of corresponding cells, calculating a correlation value, and determining whether the computed correlation value is equal to or less than a predetermined value, it is possible to detect whether a cell under observation is a living cell or debris, cell remains, an air bubble, or another piece of foreign matter. The abovementioned predetermined value is set in accordance with the cell type or activity conditions, the time interval for viewing, and other factors, and can be selected from a range of about 0.5 to 0.8, for example.

(Method for Deriving and Detecting the Degree of Activity of a Living Cell)

A texture feature value of the intracellular structure is computed for the first figure and second figure of the cell under observation, for which the rotation angle orientation is aligned. Various publicly known indicators can be used as the intracellular texture feature, examples of which are cited below. Specific indicators include (1) variance of luminance values, (2) differential sum, (3) vertical, horizontal, and rotational symmetry (correlation value), (4) directional components (Gabor filter or the like), (5) texture analysis, and the like.

(1) Variance of Luminance Values

By observing fluctuations in luminance values in a cell (inside the outermost contour), since larger values indicate fluctuation, the intensity of a body inside the cell can be known. For example, it is possible to approximate aggregates of bodies such as increases and decreases in granules, the number or size of nuclei, and unevenness due to density.

(2) Differential Sum

The edge intensity of an intracellular body can be computed by the differential (difference of luminance values in the vertical, horizontal, and diagonal directions, also including a Sobel filter or the like) with respect to a spatial direction of the luminance in the cell, and by summation, it is possible to know the increase and decrease of intracellular granules, and the number and size of nuclei. Unlike variance, this indicator is not significantly affected by unevenness due to density, and optical unevenness can be excluded.

(3) Symmetry

The degree of spatial movement or bias of intracellular bodies can be known. For example, in a case in which the nucleus in the cell is at one end of the cell and moves over time, the symmetry correlation value decreases. This is caused not only by movement of the nucleus, but also by such factors as variation of uneven luminance (density of bodies). Vertical, horizontal, and rotational symmetry correlation values are computed according to the shape of the cell.

(4) Directional Components

Line segments inside the cell are extracted by using a Gabor filter, which is a typical filter for extracting line segments and the like, or another filter in which different spatial frequencies (band-pass spectra) are extracted vertically and horizontally, and the sum thereof is used as a feature value. In the case of a Gabor filter, the filter is prepared according to a vertical, horizontal, diagonal, or other direction, and the sensitivity with respect to each direction is used as a feature value. The differential is a high-pass filter, whereas the Gabor filter is a band-pass filter, and extracts the structure of bodies which have thickness.

(5) Texture Analysis

Commonly used texture analysis is for analyzing more detailed texture patterns, unlike such simple feature values as luminance histograms, spatial coocurrence matrices, Fourier transforms (spectral intensities of spatial frequencies), or the like, and produces a multidimensional feature value in which the abovementioned matrices or distributions are handled without modification. By extracting the correlation values thereof, more detailed information can be obtained.

The difference or correlation value between the texture feature value of the first figure and the texture feature value of the second figure thus computed, or the difference or correlation value between the first figure and second figure is computed, and the time series variation thereof is derived. Specifically, the second image and first image are sequentially applied to the images of times t and t+1, t+1 and t+2, t+2 and t+3, . . . , t+m and t+n, the correlation value or difference between the texture feature value of the first figure and the texture feature value of the second figure in each image is computed, or the correlation value or difference between the first figure and the second figure is computed, and the time series variation thereof is derived.

Figure 1:
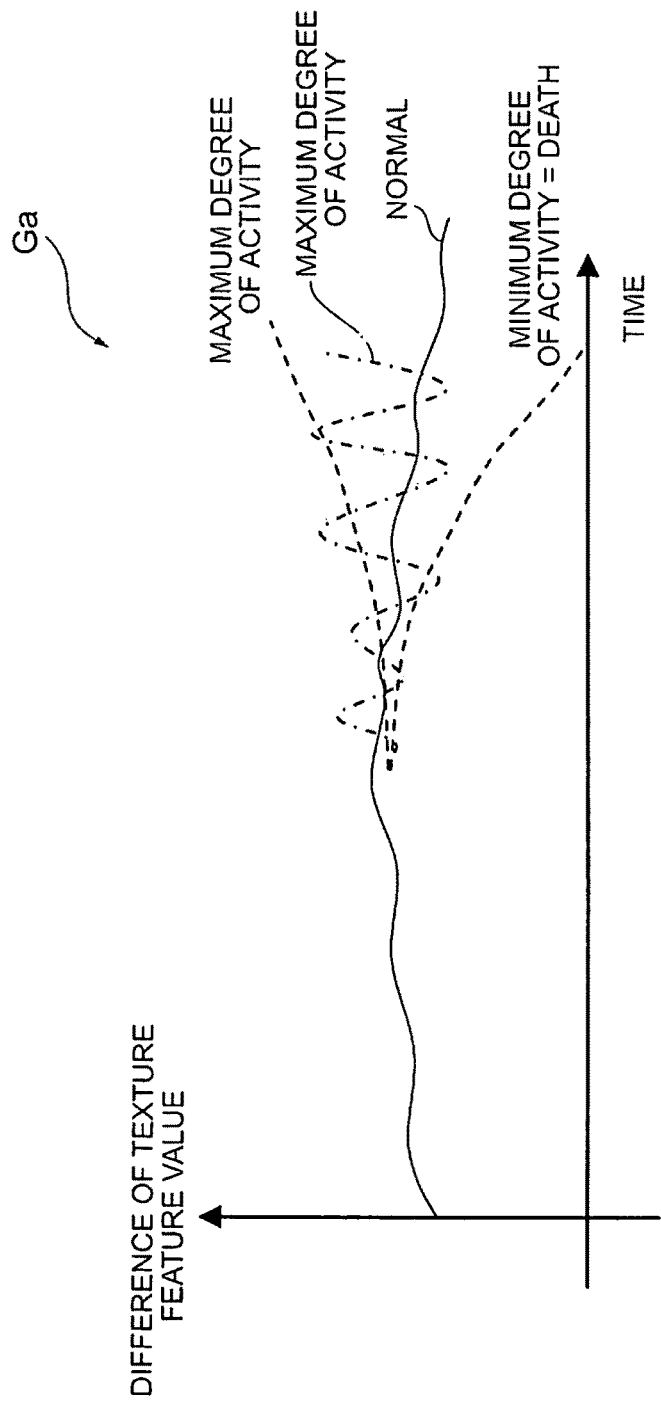
FIG. 1 is a cell activity graph showing the time series variation of the abovementioned difference, where the difference between the texture feature value of the first figure and the texture feature value of the second figure is shown on the vertical axis, and time is shown on the horizontal axis.
Figure 8:
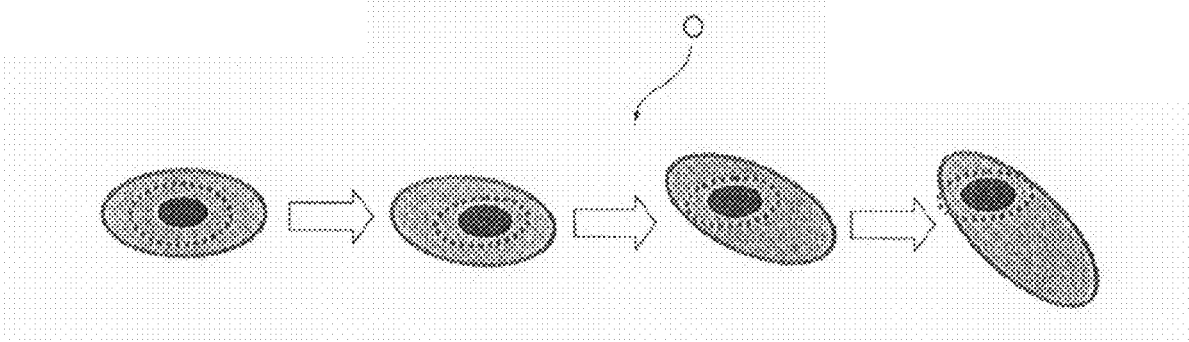
FIG. 8 is a schematic view showing an example of the change in a normal living cell over time.

FIG. 1 is a graph showing an example of the time series variation of the abovementioned difference, where the difference between the texture feature value of the first figure and the texture feature value of the second figure is shown on the vertical axis, and time is shown on the horizontal axis. In a normal living cell such as the one shown in FIG. 8, the texture feature value changes due to movement, deformation, or other action of the internal structure between the first and second figures. The difference in the texture feature value therefore smoothly fluctuates about a certain constant magnitude, as indicated by the solid line in FIG. 1.

Figure 9:
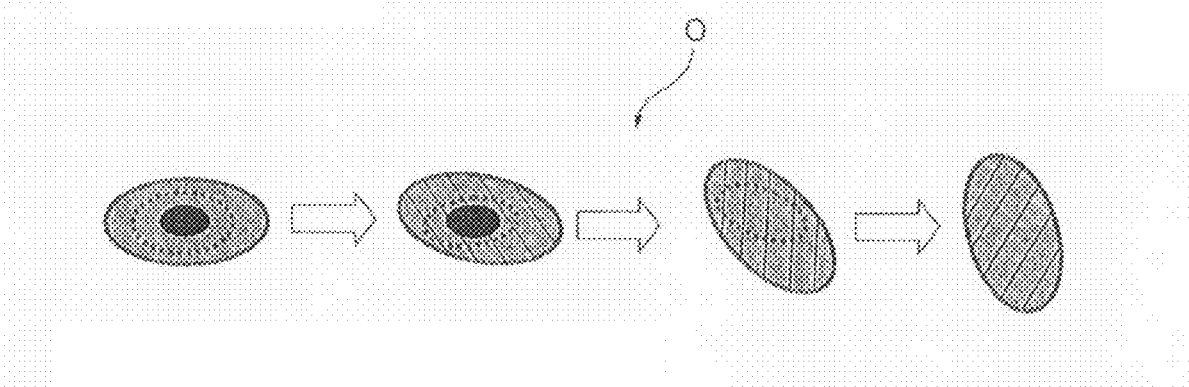
FIG. 9 is a schematic view showing an example of a change from a living cell to a dead cell over time.

In a case in which the activity of the cell under observation gradually decreases until the cell dies, as shown in FIG. 9, the movement, deformation, and other effects in the internal structure between the first and second figures decrease over time. Therefore, as indicated by the descending dotted line in FIG. 1, the difference of the texture feature value gradually decreases substantially to zero at the point of cell death, where there is no more change. In a case in which the cell enters a mitotic period, or an abnormal activity occurs, there is significant movement or change in the internal structure between the first and second figures, the difference of the texture feature value increases or varies in wide undulating fashion as indicated by the rising dotted line or the sinusoidal dashed-dotted line in FIG. 1.

Consequently, by observing the time series variation of the difference between the texture feature value of the first figure and the texture feature value of the second figure, the degree of activity of a cell under observation, which was difficult to accurately determine in the past, can be accurately and quantitatively determined.

Figure 10:
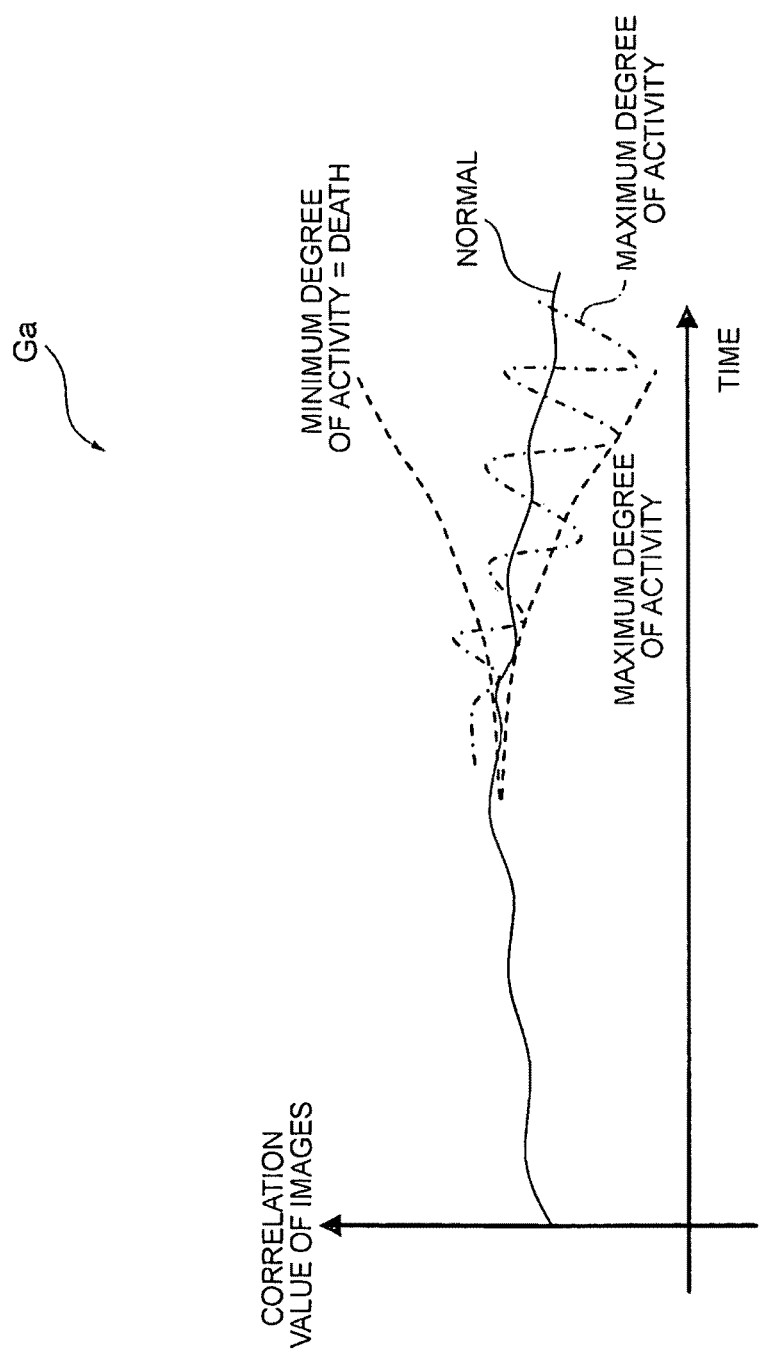
FIG. 10 is a cell activity graph showing the time series variation of the abovementioned correlation value, where the correlation value between the first figure and second figure is shown on the vertical axis, and time is shown on the horizontal axis.

A case is described above in which the difference between the texture feature value of the first figure and the texture feature value of the second figure is used, but the degree of activity can also be determined in the same manner by observing a time series variation using a correlation value of the texture feature value of the first figure and the texture feature value of the second figure, and the degree of activity can also be determined in the same manner by observing a time series variation using the difference or correlation value of the first figure and the second figure. FIG. 10 is a graph showing the time series variation of the abovementioned correlation value, where the correlation value of the first figure and the second figure is shown on the vertical axis, and time is shown on the horizontal axis.

As previously mentioned, in the case of a living cell, cell activity causes movement or deformation of the internal structure between the first and second figures. Therefore, in a normal living cell such as the one shown in FIG. 8, the texture feature varies between the first and second figures, and the correlation value of the first figure and second figure smoothly fluctuates about a certain constant magnitude, as indicated by the solid line in FIG. 10.

In a case in which the activity of the cell under observation gradually decreases to cell death (FIG. 9), since movement, deformation, and other effects in the internal structure decrease between the first and second figures, the correlation value of the first figure and second figure gradually increases to substantially a value of 1, no longer changing at cell death, as indicated by the rising dotted line in FIG. 10. In a case in which the cell enters a mitotic period, or an abnormal activity occurs, there is significant movement or change in the internal structure between the first and second figures, and the correlation value of the first figure and second figure decreases or varies in wide undulating fashion as indicated by the falling dotted line or the sinusoidal dashed-dotted line in FIG. 10.

Consequently, it is also possible to accurately and quantitatively determine the degree of activity or the state of life or death of the cell under observation in the same manner as by the time series variation of the difference of the texture feature values as described above, by observing the time series variation of the correlation value of the first figure and second figure (or the correlation value of the texture feature value of the first figure and the texture feature value of the second figure). The degree of activity of a cell under observation, which was difficult to accurately determine in the past, can thereby be accurately and quantitatively determined.

APPLICATIONS

A method for deriving and determining the degree of activity of a living cell is described above, but a specific application of the image analysis executed in the image processing device 100 of the culture viewing system BS will be described below with reference to FIG. 11. FIG. 11 is a block diagram showing the overall configuration of the image processing device 100 for executing image processing for living cell detection. The time series variation graphs shown in FIGS. 1 and 10 obtained by the determination method described above are referred to in the present Specification as "cell activity graphs," and are indicated by the reference symbol Ga.

The image processing device 100 is provided with an image storage unit 110 for sequentially storing images captured by the imaging device 55c (54c) at a predetermined time interval; an image analysis unit 120 for obtaining and analyzing the images stored by the image storage unit 110; and an output unit 130 for outputting the results of analysis by the image analysis unit 120, and is configured so as to output the degree of activity of a cell or the time series variation of the correlation value or difference derived by the image analysis unit 120 to the display panel 72 for display. In the image processing device 100, an image processing program GP set and stored in advance in the Ram 62 is read by the CPU 61, and processing based on the image processing program GP is sequentially executed by the CPU 61.

The processing by the image analysis unit 120 can be executed by reading a plurality of image data already stored in the image storage unit 110 (image storage region of the RAM 63), or by obtaining an image of the cell currently under observation from the imaging device. In the present example, a case is described in which the degree of activity of a cell included in an observation image is displayed and detected in the process of microscope viewing of the cell.

When the viewing program starts in the culture viewing system BS, a cell in a specified culture container is viewed at a predetermined time interval which is set in advance in the program. The CPU 61 operates the X, Y, and Z stages 43, 42, 41 of the conveyance unit 4 to convey the culture container 10 to be viewed from the stocker 3 to the viewing unit 5 and mount the culture container 10 on the sample stage 15, and causes the imaging device 55c to capture an observation image through the microscope viewing system 55.

The observation image captured by the imaging device 55c is stored in the image storage unit 110 together with various index data. The operations of obtaining an observation image and storing the observation image in the image storage unit 110 are repeated by the image processing device 100 at a predetermined time interval set in the viewing program.

Figure 5:
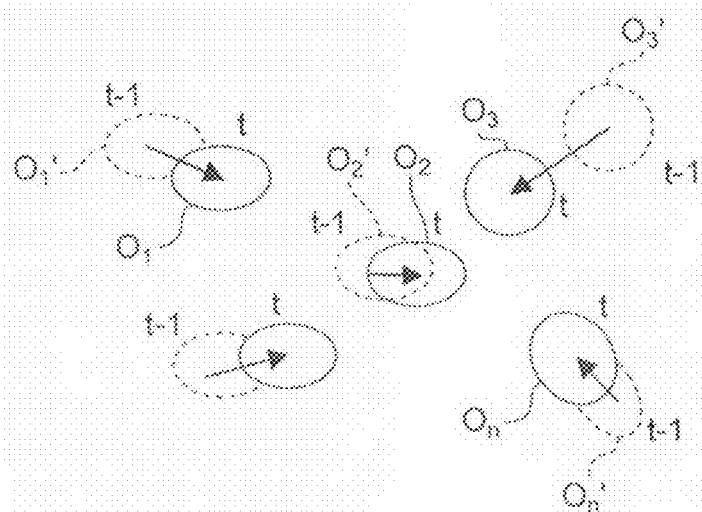
FIG. 5 is a view showing the correlation between cells included in an image at time t−1 and cells included in an image at time t.

The image analysis unit 120 executes outermost contour extraction processing as shown in FIG. 4 for the observation image (first image) of time t obtained from the imaging device 55c, and the observation image (second image) captured by the imaging device 55c at time t−1 a predetermined time before time t and stored in the image storage unit 110, applies labeling, and associates the cells $O_1, O_2, O_3, \ldots, O_n$ in the first image and the cells $O_1', O_2', O_3', \ldots, O_n'$ in the second image by nearest-neighbor association as shown in FIG. 5. The rotation angle orientations of the figures of the cells in the first image, i.e., the first figures, and the figures of the cells in the second image, i.e., the second figures, are then aligned for the associated cells.

For example, an elliptical approximation is performed for the first figure On and second figure On' of a cell to compute the major-axis direction of the ellipse, and the elliptical centers and major-axis directions of the first figure and second figure are aligned. At this time, it is sometimes the case that the major-axis direction of an ellipse has two directions to the left and right about the centroid (elliptical center), and the head and foot of the cell are oriented in opposite directions. A correlation value is therefore computed for both the 0-degree direction and the 180-degree direction about the centroid, and the rotation angle orientation is aligned with the angle having the larger correlation value. In a case in which the correlation value of the first figure and second figure whose rotation angle orientations are aligned is near 1, the cell is highly likely to be a dead cell, a piece of debris, an air bubble, or the like. Consequently, by using the abovementioned correlation value as identifying information, it is possible to promptly distinguish between a living cell and a dead cell, and the processing burden can be reduced by excluding dead cells from the subsequent processing.

The image analysis unit 120 then computes the correlation value or difference between the intracellular texture feature value of the first figure, whose rotation angle orientation is aligned, and the intracellular texture feature value of the second figure, or computes the correlation value or difference of the first figure and second figure. For example, in a case in which cell $O_3$ is selected in the operating panel 71 as the cell under observation, and the difference of the texture feature value is selected as the indicator for determining cell activity (or in a case in which such initial settings are made), the image analysis unit 120 computes the difference $D_t$ between the intracellular texture feature value of the first figure whose rotation angle orientation is aligned, and the intracellular texture feature value of the second figure, and records the difference $D_t$ as activity data of the cell $O_3$ for time t in the RAM 63. A graph frame is created in which the difference of the texture feature value is shown on the vertical axis, and time is shown on the horizontal axis, and the difference $D_t$ is plotted at the position of time t in the graph frame to create a cell activity graph. The output unit 130 outputs the cell activity graph created by the image analysis unit 120 and displays the cell activity graph on the display panel 72.

The image analysis unit 120 then sequentially repeats the processing described above each time an observation image is captured by the imaging device 55c. In other words, the difference $D_{t+1}$ of the texture feature value at time t+1 of the cell $O_3$ under observation is computed from the first image of time t+1 obtained from the imaging device 55c, and the second image of time t stored in the image storage unit 110, and the difference $D_{t+1}$ is plotted at the position of time t+1 in the cell activity graph. The output unit 130 outputs a cell activity graph that is updated each time the data are updated in the image analysis unit 120, and displays the cell activity graph on the display panel 72.

A continuous cell activity graph Ga such as the one shown in FIG. 1 is thereby displayed on the display panel 72 as the amount of viewing data increases, making it possible to comprehend the time series variation of the difference of the texture feature value of the cell $O_3$ under observation after the start of the cell viewing program.

Consequently, by viewing the cell activity graph Ga, the degree of activity of the cell under observation can be determined as described above in the description of the determination method. For example, in a case in which the cell activity graph Ga displayed on the display panel 72 shows a feature such as that indicated by the solid line in FIG. 1, a determination can be made that the activity of the cell $O_3$ under observation is stable. In the case of a features such as the one indicated by the falling dotted line in FIG. 1, the activity of the cell $O_3$ under observation is determined to be decreasing to cell death, and in the case of features such as the one indicated by the rising dotted line or the widely undulating dashed-dotted line in FIG. 1, the cell $O_3$ under observation can be determined to have entered a mitotic period or other state of increased activity.

A configuration may be adopted in which the image analysis unit 120 determines that cell activity is reduced and outputs activity reduction information in a case in which the difference of the texture feature value in the cell activity graph Ga shown in FIG. 1 decreases to or below a predetermined value, or the reduction rate is equal to or higher than a predetermined value, and the message "Cell Activity Reduced" or a graphic is lit or displayed blinking in the cell activity graph Ga displayed by the display panel 72, or a line of the graph is displayed blinking in red, for example. In the same manner, in a case in which the difference of the texture feature value increases to or above a predetermined value, or the increase rate is equal to or higher than a predetermined value, the message "Cell Activity Increased" or a graphic may be lit or displayed blinking in the cell activity graph Ga, or a line of the graph may be displayed blinking in blue. Through such a configuration, it is possible to immediately and correctly recognize whether the degree of activity of a cell is increased or decreased without misreading the display.

The above description is of a case in which the difference of the texture feature value is selected as the indicator for determining cell activity (or a case in which such initial settings are made), but cell activity can be determined in the same manner in a case in which the difference of the first figure and the second figure is selected. Application can be made in the same manner in a case in which the correlation value of the texture feature value or the correlation value of the first figure and second figure is selected as the indicator for determining cell activity (or in a case in which such initial settings are made), and the state of life or death or the degree of activity of the cell under observation can be determined by displaying the time series variation of the correlation value. As is apparent from comparing FIG. 1 with FIG. 10, in a case in which the correlation value is used as the indicator for determining cell activity, the cell activity is in a reduced state when the correlation value has an increasing tendency, and the cell activity is in an increased state when the correlation value has a decreasing tendency. In other words, the change in the correlation value displayed on the graph is inversely related to the state of cell activity, and differs from the intuitive image. In this regard, by adopting a configuration in which the image analysis unit 120 determines the cell activity state and causes the messages "Cell Activity Reduced" and "Cell Activity Increased" or a graphic to be lit or displayed blinking on the cell activity graph Ga, or displays the graph using different colors, instinctive false recognition can be prevented, and the state of the cell can be correctly recognized.

A specific cell $O_3$ is selected in the operating panel 71 In the case described above, but a configuration may be adopted in which there is no cell selection operation, and the image analysis unit 120 executes the processing described above for all of the cells included in the field of view, and the output unit 130 outputs an individual cell activity graph for each cell $O_1$, $O_2, O_3, \ldots, O_n$ or a graph in which the cell activity graphs are displayed in overlapping fashion, a graph of average values of all or a portion of the cells in the field of view, the results of determining the degree of activity, or other results. A configuration may be adopted in which cell activity detection data such as described above outputted from the output unit 130 are transmitted to an externally connected computer or the like via the communication unit 65, and the same image is displayed, or the data are used as basic data for executing cell movement analysis, cell tracking, or other processing. An observer can thereby determine the degree of activity of a cell included in an image which is being viewed (or in an observation image already obtained and stored in the RAM 63), by referencing the cell activity graph displayed on the display panel 72, or a cell activity graph Ga displayed by the display device of the external connected computer or the like.

Through the method for detecting a cell state, and the image processing device such as described above, the degree of activity of a cell can be quantitatively determined by the time series variation of the correlation value or difference of texture feature values, or the correlation value or difference of the first figure and second figure of cells under observation, and the activity of a cell can be accurately determined merely from an observation image captured and obtained by an imaging device.

What is claimed is:

1. A method for detecting a cell state, comprising:
sequentially obtaining first image data and second image data for a cell under observation by using an imaging device at a predetermined time interval;
aligning rotation angle orientations corresponding to the first and second image data for the cell under observation, the rotation angle orientations being obtained by calculating the rotation angles of axes passing through the centroid of the cell under observation in order to align the orientations on the image plane of the cell under observation when the first image data is obtained and the cell under observation when the second image data is obtained;
extracting a variation amount between an intracellular texture feature value of the cell under observation in the first image data and an intracellular texture feature value of the cell under observation in the second image data, the rotation angle orientations being aligned; and
detecting a degree of activity of the cell under observation on the basis of a time series variation of the extracted variation amount.

2. The method for detecting a cell state according to claim 1, wherein the time series variation of the extracted variation amount is calculated by sequentially computing a correlation value or difference between the intracellular texture feature value of the cell under observation when the first image data is obtained and the intracellular texture feature value of the cell under observation when the second image data is obtained.

3. The method for detecting a cell state according to claim 2, wherein a determination is made that the degree of activity of the cell under observation is reduced in a case in which the difference tends to decrease, and a determination is made that the degree of activity of the cell under observation is increased in a case in which the difference tends to increase.

4. The method for detecting a cell state according to claim 2, wherein a determination is made that the degree of activity of the cell under observation is reduced in a case in which the correlation value tends to increase, and a determination is made that the degree of activity of the cell under observation is increased in a case in which the correlation value tends to decrease.

5. An image processing device for cell viewing, comprising:
- an imaging device to capture an image of a cell under observation by sequentially obtaining first image data and second image data for the cell under observation at a predetermined time interval;
- a memory; and
- a processor coupled to the memory and configured to execute operations including:
  - aligning rotation angle orientations corresponding to the first and second image data for the cell under observation, the aligning including calculating the rotation angles of axes passing through the centroid of the cell under observation in order to align the orientations on the image plane of the cell under observation when the first image data is obtained and the cell under observation when the second image data is obtained;
  - extracting a variation amount between an intracellular texture feature value of the cell under observation in the first image data and an intracellular texture feature value of the cell under observation in the second image data, the rotation angle orientations being aligned; and
  - detecting a degree of activity of the cell under observation on the basis of a time series variation of the extracted variation amount.

6. The image processing device for cell viewing according to claim 5, wherein the extracting calculates the time series variation of the extracted variation amount by sequentially computing a correlation value or difference between the intracellular texture feature value of the cell under observation when the first image data is obtained and the intracellular texture feature value of the cell under observation when the second image data is obtained.

7. The image processing device for cell viewing according to claim 6, wherein the extracting detects the degree of activity of the cell under observation on the basis of the time series variation of the correlation value or the difference, and outputs the degree of activity of the cell under observation that is detected.

8. The image processing device for cell viewing according to claim 7, wherein extracting determines that the degree of activity of the cell under observation is reduced in a case in which the difference tends to decrease, and determines that the degree of activity of the cell under observation is increased in a case in which the difference tends to increase.

9. The image processing device for cell viewing according to claim 7, wherein the extracting determines that the degree of activity of the cell under observation is reduced in a case in which the correlation value tends to increase, and determines that the degree of activity of the cell under observation is increased in a case in which the correlation value tends to decrease.

10. Apparatus to detect a cell state, comprising:
- an imaging device to sequentially capture first and second images of a cell under observation and to provide first image data and second image data respectively corresponding to the first and second images; and
- an image analysis unit using the first and second image data to align rotation angle orientations corresponding to the first and second images, to extract a variation amount between an intracellular texture feature value of the cell under observation in the first image and an intracellular texture feature value of the cell under observation in the second image with the rotation angle orientations aligned, and to detect a degree of activity of the cell under observation on the basis of a time series variation of the extracted variation amount, the rotation angle orientations being obtained by calculating the rotation angles of axes passing through the centroid of the cell under observation in order to align the orientations on the image plane of the cell under observation when the first image data is obtained and the cell under observation when the second image data is obtained.

11. The apparatus according to claim 10, further comprising:
- an output unit to output data corresponding to a cell activity graph corresponding to the degree of activity detected by the image analysis unit; and
- a display panel to display the cell activity graph.

* * * * *

UNITED STATES PATENT AND TRADEMARK OFFICE
CERTIFICATE OF CORRECTION

PATENT NO. : 8,902,306 B2  
APPLICATION NO. : 12/929369  
DATED : December 2, 2014  
INVENTOR(S) : Mimura et al.

Page 1 of 1

It is certified that error appears in the above-identified patent and that said Letters Patent is hereby corrected as shown below:

On the title page item [56], Column 2, line 4, delete "Apoptoic" and insert -- Apoptotic --, therefor.

Signed and Sealed this  
Twenty-third Day of June, 2015

Michelle K. Lee  
*Director of the United States Patent and Trademark Office*